US012667446B2

(12) United States Patent
Millar

(10) Patent No.: US 12,667,446 B2
(45) Date of Patent: Jun. 30, 2026

(54) APPARATUS FOR HOLDING TRANSDUCERS

(71) Applicant: Allen Currie Millar, Rogers, AR (US)

(72) Inventor: Allen Currie Millar, Rogers, AR (US)

( * ) Notice: Subject to any disclaimer, the term of this patent is extended or adjusted under 35 U.S.C. 154(b) by 488 days.

(21) Appl. No.: 18/125,983

(22) Filed: Mar. 24, 2023

(65) Prior Publication Data

US 2024/0315800 A1    Sep. 26, 2024

(51) Int. Cl.
*A61B 90/57*    (2016.01)

(52) U.S. Cl.
CPC ........ *A61B 90/57* (2016.02); *A61B 2090/571* (2016.02)

(58) Field of Classification Search
CPC .......................... A61B 90/57; A61B 2090/571
See application file for complete search history.

(56) References Cited

U.S. PATENT DOCUMENTS

| | | | |
|---|---|---|---|
| 1,799,079 A | 3/1931 | Bemis | |
| 2,191,782 A * | 2/1940 | Ernest | A61G 7/05 |
| | | | 24/339 |
| 2,486,276 A | 10/1949 | Ap | |
| 2,942,314 A * | 6/1960 | Debner | F16B 7/0433 |
| | | | 24/339 |
| 3,006,231 A * | 10/1961 | Kahn | F16B 5/0291 |
| | | | 470/23 |
| 4,227,667 A * | 10/1980 | Dickerson | A61M 5/1415 |
| | | | 24/339 |
| 4,702,448 A | 10/1987 | LoJacono | |
| 4,821,988 A | 4/1989 | Jimenez | |

| | | | |
|---|---|---|---|
| 4,861,081 A * | 8/1989 | Satoh | E05B 79/12 |
| | | | 292/336.3 |
| 4,953,819 A | 9/1990 | Davis | |
| 4,997,147 A * | 3/1991 | Velke, Sr. | F16L 3/1215 |
| | | | 248/50 |
| 5,351,920 A | 10/1994 | Decky | |
| 5,358,205 A | 10/1994 | Starkey | |
| 5,417,395 A | 5/1995 | Fowler et al. | |
| 5,566,676 A | 10/1996 | Rosenfeldt et al. | |
| 5,588,166 A | 12/1996 | Burnett | |
| D414,872 S | 10/1999 | Doyle | |
| 6,409,131 B1 | 6/2002 | Bentley et al. | |
| 6,588,716 B1 | 7/2003 | Heid | |
| 6,631,876 B1 * | 10/2003 | Phillips | F16B 2/22 |
| | | | 248/74.2 |
| 6,802,484 B1 | 10/2004 | Kiley | |
| 6,969,031 B2 | 11/2005 | Ugnet | |
| 7,111,812 B2 | 9/2006 | Shannon | |
| 7,294,789 B1 * | 11/2007 | Watthanasintham | |
| | | | F16L 3/1215 |
| | | | 174/64 |

(Continued)

FOREIGN PATENT DOCUMENTS

| | | | |
|---|---|---|---|
| CN | 111420161 | 7/2020 | |
| WO | WO-2023027600 A1 * | 3/2023 | A61M 25/02 |

OTHER PUBLICATIONS

International Search Report and Written Opinion of PCT/US2024/020499, Millar, Allen Currie.

(Continued)

*Primary Examiner* — Monica E Millner

(74) *Attorney, Agent, or Firm* — Dennis D. Brown; Brown Patent Law, P.L.L.C.

(57) ABSTRACT

An apparatus and method for securing one or multiple pressure transducers on an IV pole.

7 Claims, 8 Drawing Sheets

(56) References Cited

U.S. PATENT DOCUMENTS

| | | | |
|---|---|---|---|
| 7,533,854 | B2 | 5/2009 | Aube |
| 8,348,072 | B2 | 1/2013 | Whitehall |
| D678,533 | S | 3/2013 | Bemstein |
| 8,602,365 | B2 * | 12/2013 | Neace ...................... H02G 3/32 |
| | | | 248/692 |
| D734,305 | S | 7/2015 | Wengreen |
| D737,435 | S | 8/2015 | Ha |
| 9,179,208 | B2 | 11/2015 | Hiderman |
| 9,198,727 | B1 | 12/2015 | Samuels |
| 9,291,305 | B2 | 3/2016 | Brehm |
| D791,965 | S | 7/2017 | Ochranek |
| D837,367 | S | 1/2019 | Reaux |
| 10,190,609 | B2 | 1/2019 | Turturro et al. |
| 10,264,736 | B2 | 4/2019 | Rider |
| D886,295 | S | 6/2020 | Doiley |
| 10,694,986 | B2 | 6/2020 | Hoan et al. |
| 10,799,311 | B2 | 10/2020 | Loui |
| 10,828,472 | B2 | 11/2020 | Kappler |
| 10,835,666 | B2 | 11/2020 | Amir |
| D904,859 | S | 12/2020 | Mulvoy |
| D915,603 | S | 4/2021 | Stalter |
| D922,793 | S | 6/2021 | Lai |
| 11,123,617 | B2 | 9/2021 | Fulford |
| D943,765 | S | 2/2022 | Griffin |
| D946,153 | S | 3/2022 | Schafer |
| 11,400,208 | B2 * | 8/2022 | Millar .................. A61M 5/1417 |
| 11,690,951 | B1 * | 7/2023 | Hartman ............. A61M 5/1415 |
| | | | 604/508 |
| 12,098,743 | B2 * | 9/2024 | Tutino ....................... E04B 9/20 |
| 2005/0116126 | A1 | 6/2005 | Ugent |
| 2008/0011907 | A1 | 1/2008 | Jacobsma |
| 2008/0143222 | A1 | 6/2008 | Greiner |
| 2013/0181100 | A1 | 7/2013 | Blankenship |
| 2014/0209550 | A1 | 7/2014 | Pryor et al. |
| 2014/0259557 | A1 | 9/2014 | Egan |
| 2015/0115123 | A1 | 4/2015 | Ng |
| 2015/0157522 | A1 | 6/2015 | Blankenship et al. |
| 2018/0064502 | A1 | 3/2018 | Shamir |
| 2018/0128421 | A1 | 5/2018 | Hiderman |
| 2018/0335177 | A1 | 11/2018 | Black |
| 2021/0321770 | A1 | 10/2021 | Blewett et al. |
| 2022/0111141 | A1 | 4/2022 | Millar |

OTHER PUBLICATIONS

European Search Report for European Application No. 21203989. 5-1122; Apr. 4, 2022.
Edwards; Pressure Monitoring Accessory, Model: TCLIP05; Page from Instruction Book.

* cited by examiner

1

APPARATUS FOR HOLDING TRANSDUCERS

FIELD OF THE INVENTION

The present invention relates to devices and methods for holding transducers and other articles on IV poles.

BACKGROUND OF THE INVENTION

Pressure transducers are used during surgical procedures, in intensive care units, and medical settings to monitor a variety of patient pressures, such as blood, central venous, pulmonary artery, and intracranial. Pressure transducers must be leveled to the patient's heart so the transducer can be zeroed to provide accurate pressure readings. Transducers frequently need to be moved up and down the IV pole. A need exists for an improved apparatus and method for holding pressure transducers, and other devices, which (a) reduces clutter in the treatment area, (b) enhances the accessibility of the devices, (c) preserves space for additional equipment, (d) safely secures and protects the devices and other equipment, (e) can be cleaned and sanitized for reuse, and (f) is easy and inexpensive to install and use.

IV (intravenous) poles are used in operating rooms, cardiac catheterization labs, endoscopic labs, intensive care units, and in other medical treatment areas and facilities for hanging fluid bags, bottles, and other containers for intravenous therapies. In addition, devices have also been manufactured for attaching transducers on IV poles. Prior devices (a) have been large, (b) have extended away from the IV pole causing other IV tubing and cables to be tangled in the transducers, and (c) have been costly to manufacture.

Consequently, in addition to the need for an improved apparatus and method for holding pressure transducers which will provide the benefits listed above, the improved apparatus and method will preferably also (i) allow multiple pressure transducers to be conveniently held on an IV pole, (b) have a smaller physical profile on the IV pole than devices previously used for holding pressure transducers on IV poles, (c) be easier to move up and down the IV pole, and (d) be less costly to manufacture and use than the prior devices.

SUMMARY OF THE INVENTION

The present invention provides an improved apparatus and method for holding one or multiple transducers on an IV pole. The improved apparatus and method satisfy the needs and alleviate the problems discussed above. The improved apparatus is more stable and less costly to manufacture and purchase than the prior holding devices. In addition, the improved apparatus is simple to install, has a smaller physical profile, can be more easily moved up and down the pole, can be easily cleaned and sanitized for reuse, and is highly effective for: (a) reducing clutter in the treatment area, (b) enhancing the accessibility of the transducers, (c) preserving space for other equipment, and (d) safely securing and protecting the transducers or other equipment.

In one aspect, there is provided an apparatus, for holding one or more transducers on an IV pole, which preferably comprises: (i) a longitudinal axis; (ii) a U-shaped collar which is receivable on the IV pole, the U-shaped collar having an open top and an open bottom through which the longitudinal axis extends, a closed inner end which extends partially around the longitudinal axis, an open outer end through which the IV pole is receivable, a first arm which extends from a first side of the closed inner end to the open outer end, and a second arm, opposite the first arm, which extends from a second side of the closed inner end to the open outer end; (iii) a second collar which is receivable on the IV pole and extends partially around the longitudinal axis, the second collar having an open top and an open bottom through which the longitudinal axis extends and a side opening through which the IV pole is receivable; (iv) a connecting arm which extends longitudinally from the U-shaped collar to the second collar; (v) a first transducer holder on the first arm of the U-shaped collar; and (vi) a second transducer holder on the second arm of the U-shaped collar. The second collar can be positioned longitudinally below or above the U-shaped collar and is preferably positioned below the U-shaped collar.

In another aspect, there is provided an apparatus, for holding one or more transducers on an IV pole, which preferably comprises: (a) a longitudinal axis; (b) a first collar which is receivable on the IV pole and extends partially around the longitudinal axis, the first collar having an open top and an open bottom through which the longitudinal axis extends and a side opening through which the IV pole is receivable; (c) a second collar which is receivable on the IV pole and extends partially around the longitudinal axis, the second collar having an open top and an open bottom through which the longitudinal axis extends and a side opening through which the IV pole is receivable; (d) a connecting arm which extends longitudinally from the first collar to the second collar; and (e) one or more transducer holders on an exterior of the first collar. The second collar can be positioned longitudinally below or above the first collar.

In yet another aspect, each of the one or more transducer holders preferably comprises (i) an upwardly extending left bracket and (ii) an upwardly extending right bracket. The upwardly extending left bracket preferably comprises a left bracket slot which has an open upper end and a closed lower end. Similarly, the upwardly extending right bracket preferably comprises a right bracket slot which has an open upper end and a closed lower end, wherein the left bracket slot faces the right bracket slot.

Further aspects, features and advantages of the present invention will be apparent to those in the art upon examining the accompanying drawings and upon reading the following Detailed Description of the Preferred Embodiments.

DETAILED DESCRIPTION OF THE PREFERRED EMBODIMENTS

Figure 1:
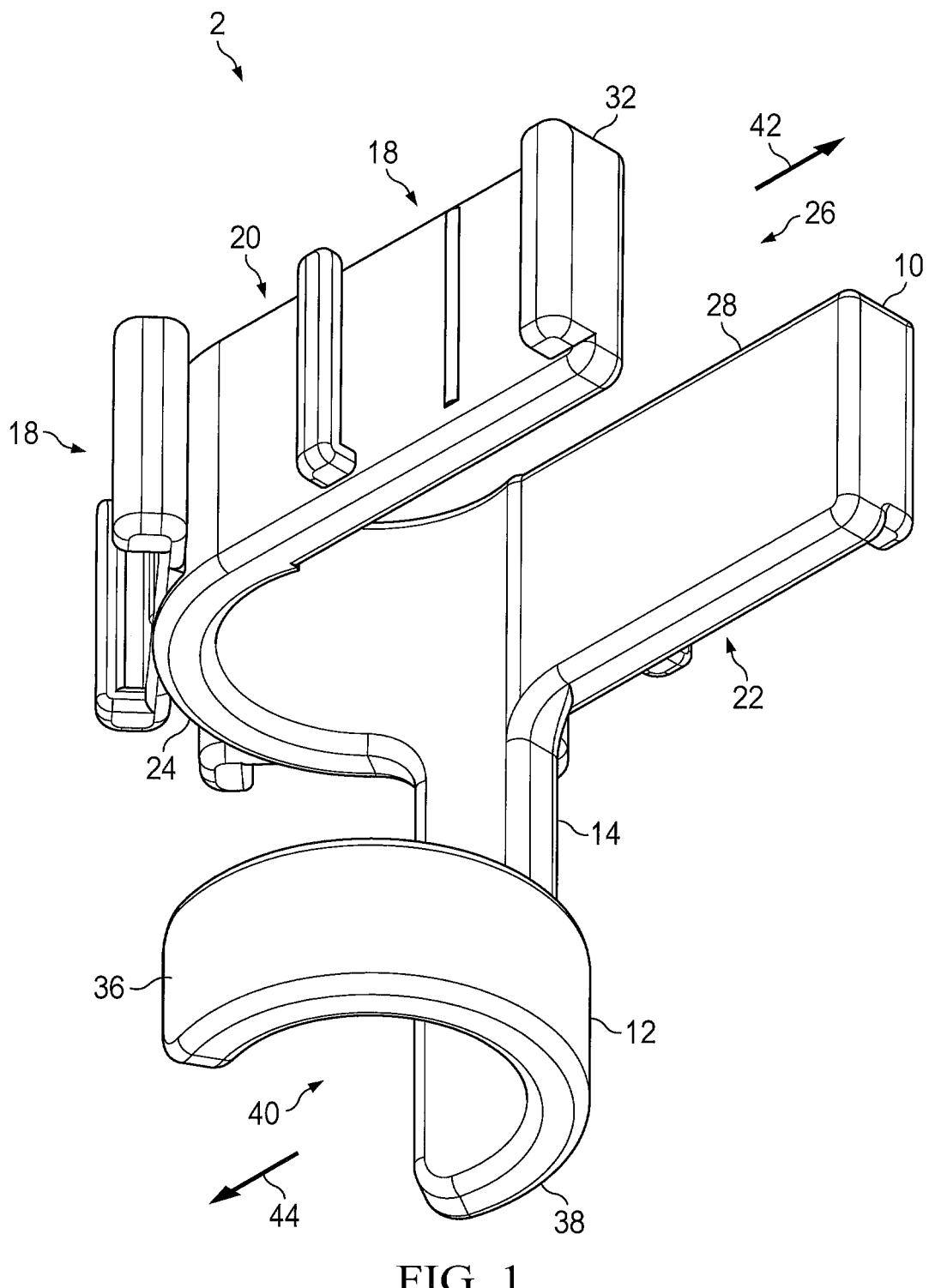
FIG. 1 is a perspective view of an embodiment 2 of the apparatus provided by the present invention for holding pressure transducers on an IV pole.
Figure 2:
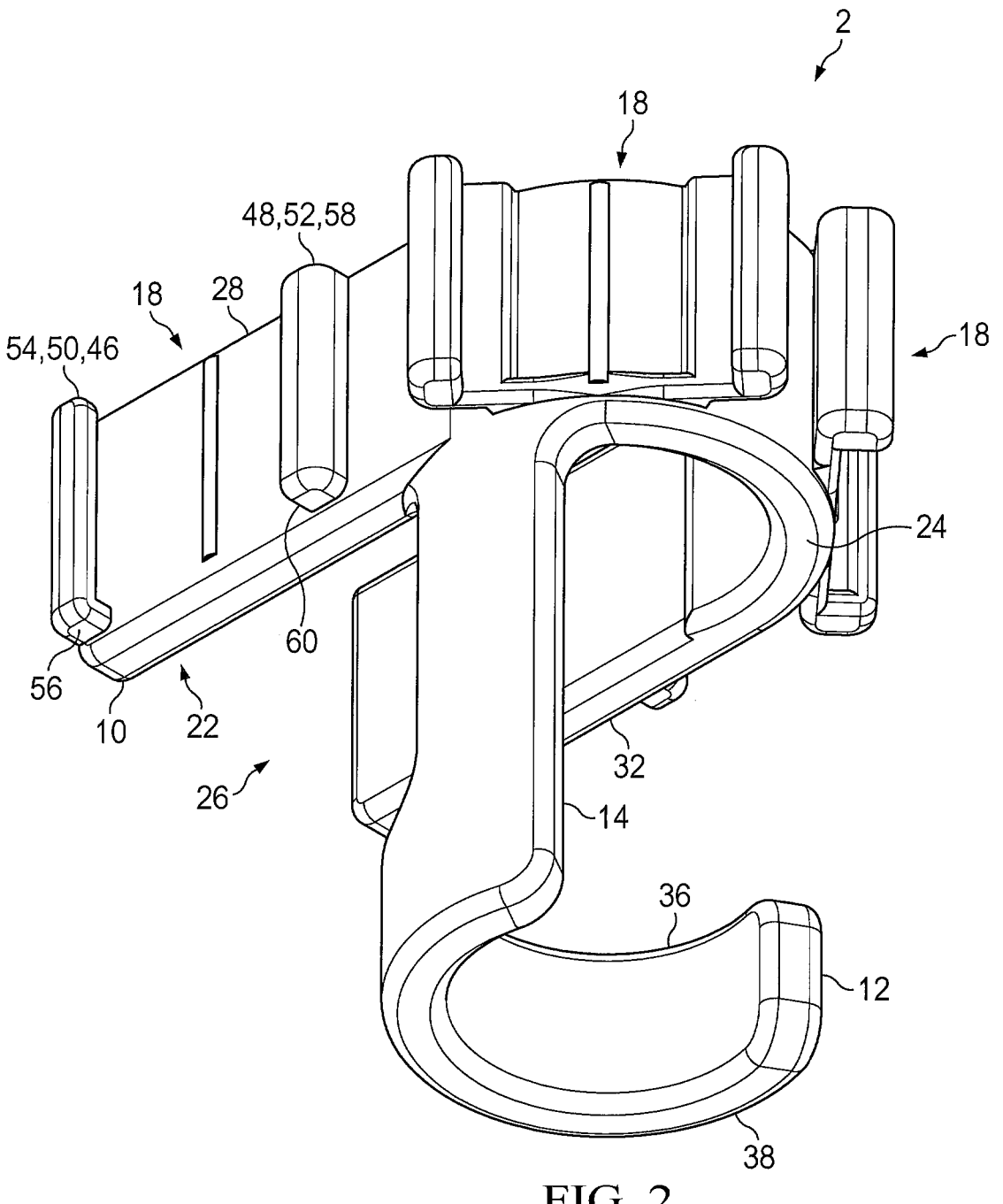
FIG. 2 is another perspective view of the inventive transducer holding apparatus 2.
Figure 3:
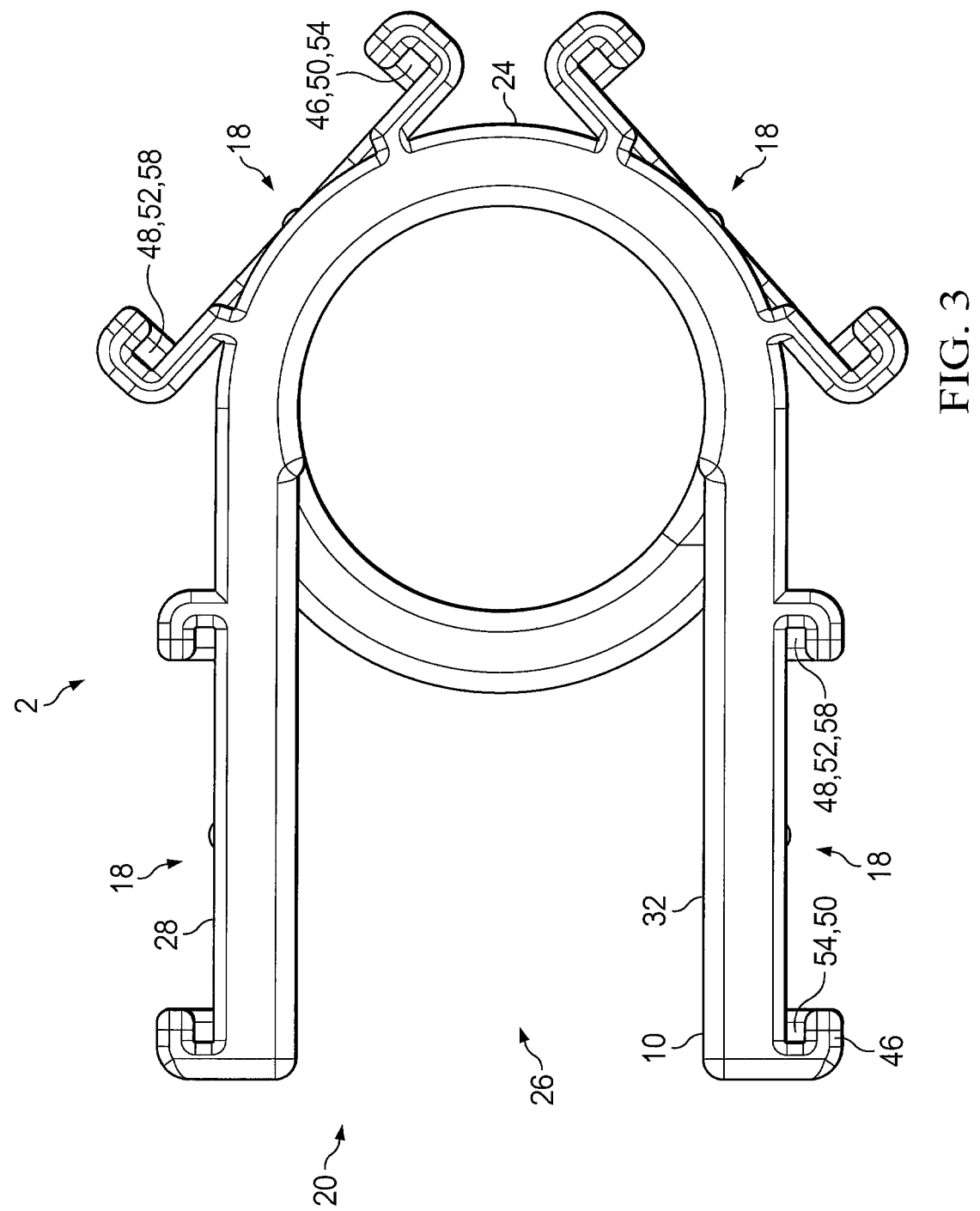
FIG. 3 is a top view of the inventive transducer holding apparatus 2.
Figure 4:
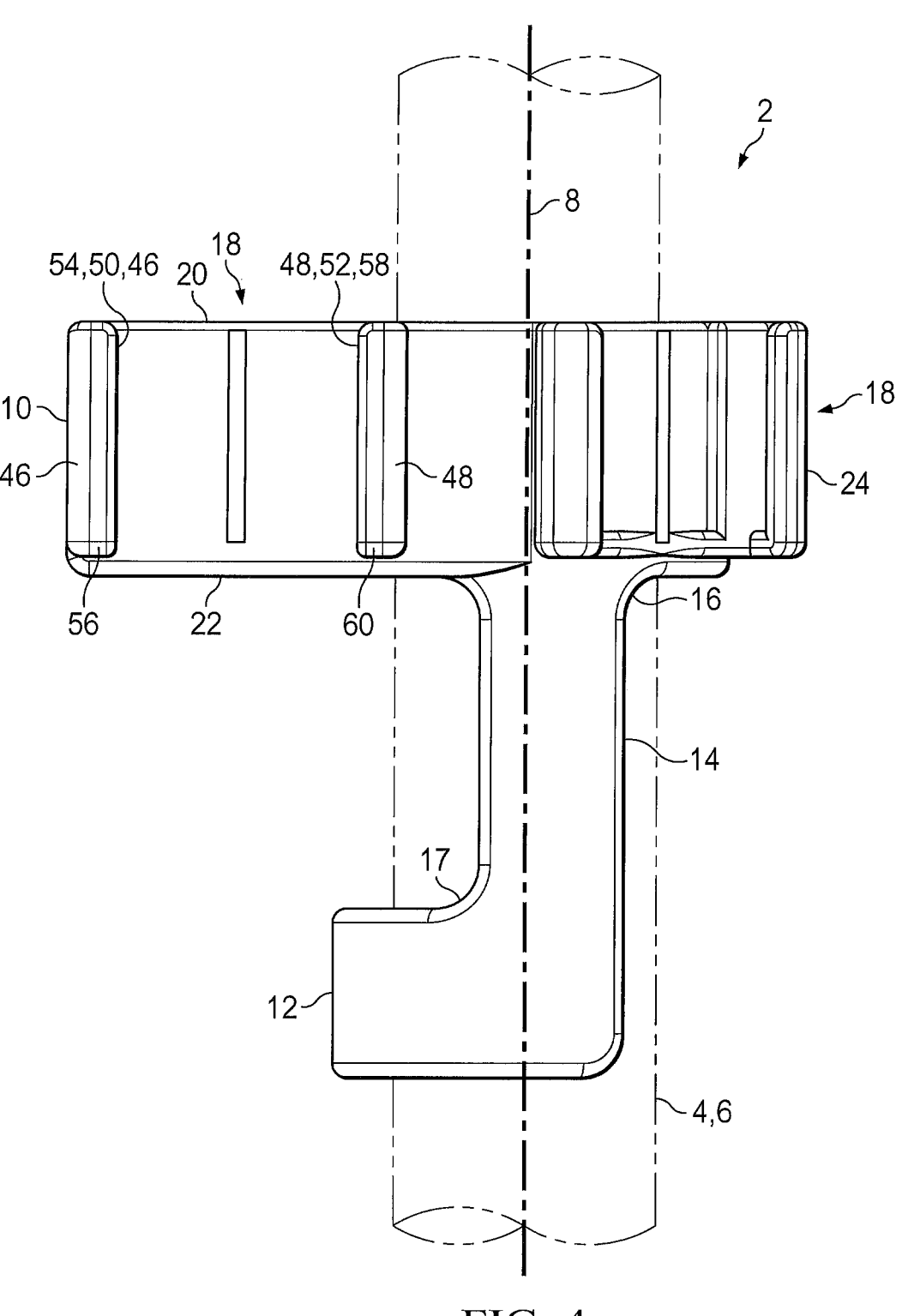
FIG. 4 is an elevational side view of the inventive transducer holding apparatus 2.
Figure 5:
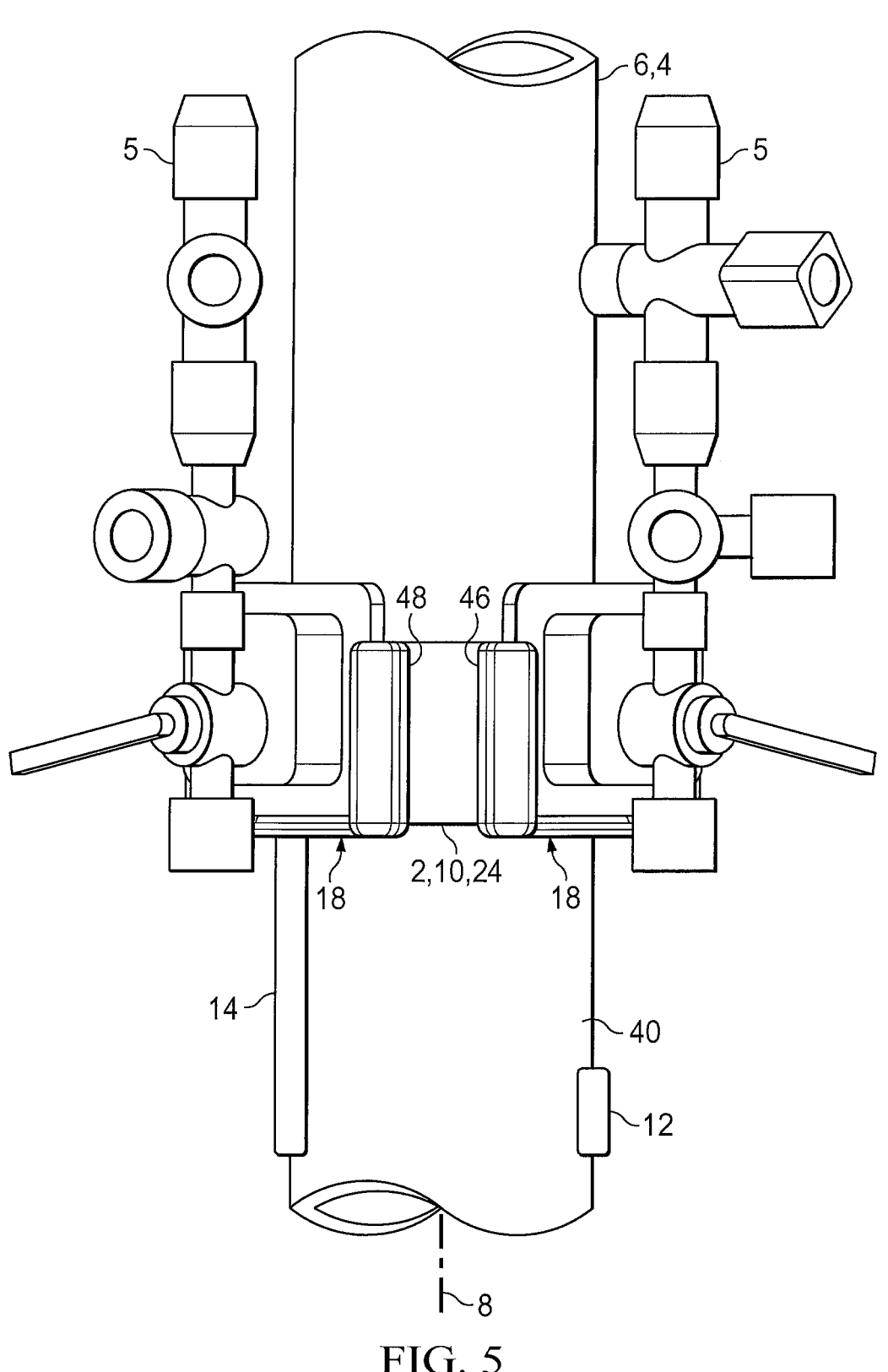
FIG. 5 is an elevational rear view of the inventive transducer holding apparatus 2.

An embodiment 2 of the inventive apparatus for holding pressure transducers 5 on an IV pole 4 in illustrated in FIGS. 1-5. The holding apparatus 2 is removably securable on the IV pole apparatus 4 for cleaning, reuse, and/or transfer to a different IV pole 4.

The IV pole apparatus 4 can be any type of IV pole apparatus which is known in the art. The IV pole apparatus 4 will typically comprise: a weighted base with wheels; a lower pole segment which extends upwardly from the weighted base; an upper pole segment 6 which is slideably received in the lower pole segment so that the upper pole segment telescopingly extends upwardly through the upper end of the lower pole segment; a locking collar on the upper end of the lower pole segment for releasably locking the upper pole segment 6 at a desired height selected by the user; and a set of hooks at the top of the upper pole segment 6 for hanging bags, bottles, or other containers containing fluids used for intravenous medical therapies.

The holding apparatus 2 preferably comprises: a longitudinal axis 8; a U-shaped collar 10 through which the IV pole 6 is removably received; a second collar 12 through which the IV pole 6 is removably received; a longitudinally extending connecting arm 14 having an end 16 which is connected to the U-shaped collar 10 and an opposite end 17 which is connected to the second collar 12; and one or more, preferably a plurality, of transducer holders 18 which is/are provided on the U-shaped collar 10.

Although other fabrication techniques can alternatively be used, the holding apparatus 2 is preferably a unitary molded structure which is formed of a non-porous plastic material. The plastic material will preferably be both (a) sufficiently flexible for placing the inventive holding apparatus 2 on the IV pole 6 and (b) sufficiently resilient for tightly gripping the IV pole 6 when the holding apparatus 2 is holding one or multiple transducers 5.

The U-shaped collar 10 of the inventive holding apparatus 2 has: an open top 20 and an open bottom 22 through which the longitudinal axis 8 and the IV pole 6 extend; a closed, preferably semicircular, inner end 24 which extends partially around the longitudinal axis 8 and the IV pole 6; an open outer end 26 through which the IV pole 6 is receivable; a first arm 28 which extends from one side of the closed inner end 24 to the open outer end 26; and a second arm 32 which extends from the other side of the closed inner end 24 to the open outer end 26. The first and second arms 28 and 30 can be angled toward or away from each other but will preferably be parallel.

The closed inner end 24 of the U-shaped collar 10 preferably extends from about 180° to about 240° (i.e., within ±5°) around both (i) the longitudinal axis 8 of the inventive holder 2 and (ii) the IV pole 6. The closed inner end 24 of the U-shaped collar 10 more preferably extends about 180° (i.e., 180°±5°) around the longitudinal axis 8 and the IV pole 6.

The second collar 12 of the inventive holding apparatus 2 is preferably a C-shaped semicircular collar which extends partially around the longitudinal axis 8 and the IV pole 6. The second collar 12 can be positioned longitudinally below or above the U-shaped collar 10 and is preferably positioned below the U-shaped collar 10. The second collar 12 preferably comprises an open top 36 and an open bottom 38, through which the longitudinal axis 8 and the IV pole 6 extend, and a side opening 40 for removably receiving the IV pole 6. The second collar 12 preferably extends from about 170° to about 320° (i.e., within ±5°) around both (i) the longitudinal axis 8 of the inventive holder 2 and (ii) the IV pole 6. The second collar 12 more preferably extends from about 180° to about 320° (i.e., within ±5°), or from about 180° to about 240°, around the longitudinal axis 8 and the IV pole 6.

The open outer end 26 of the U-shaped collar 10 faces in a first radial direction 42 with respect to the longitudinal axis 8. The side gap opening 40 of the second collar 12 faces in a second radial direction 44, with respect to the longitudinal axis 8, which is preferably different from the first radial direction 42. The second radial direction 44 is preferably about 180° (i.e., 180°±5°) opposite the first radial direction 42. In addition, the connecting arm 14 of the inventive holding apparatus 2 preferably extends longitudinally along only one side of the holding apparatus 2 and does not block or interfere with either the open outer end 26 of the U-shaped collar 10 or the side gap opening 40 of the second collar 12. This configuration allows the inventive holding apparatus 2 to be snapped onto the IV pole 6 without disassembling the IV pole apparatus 4.

As noted above, the inventive holding apparatus 2 preferably comprises a plurality of transducer holders 18 on the U-shaped collar 10. The transducer holders 18 preferably include: at least one transducer holder 18 formed or otherwise provided on the first arm 28, more preferably on the exterior of the first arm 28; at least one transducer holder 18 formed or otherwise provided on the second arm 32, more preferably on the exterior of the second arm 32; and at least one transducer holder 18, more preferably two holders 18, on the exterior of the closed inner end 24 of the U-shaped collar 10.

Each of the transducer holders 18 preferably comprises an upwardly extending left bracket 46 and an upwardly extending right bracket 48. The left and right brackets 46 and 48 are preferably parallel to the longitudinal axis 8. The upwardly extending left bracket 46 has an upwardly extending left bracket slot 50 which faces a corresponding, upwardly extending right bracket slot 52 provided by the upwardly extending right bracket 48. The upwardly extending left bracket slot 50 has an open upper end 54 and a closed lower end 56. The upwardly extending right bracket slot 52 has an open upper end 58 and a closed lower end 60.

Figure 6:
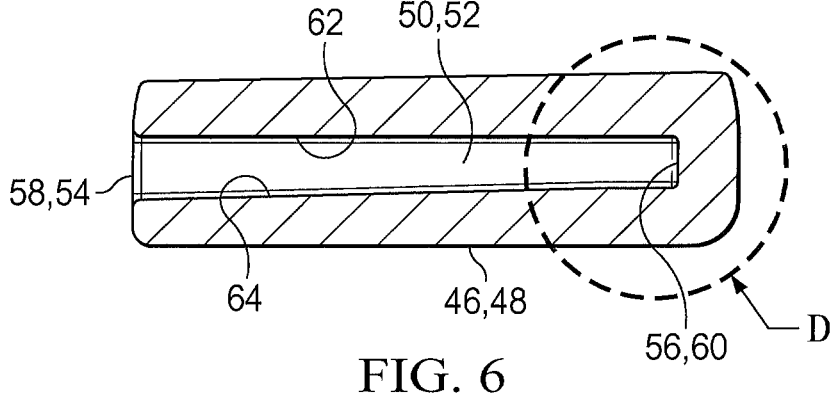
FIG. 6 is a cross sectional view of an upwardly extending left bracket 46 or an upwardly extending right bracket 48 of a transducer holding structure 18 of the inventive transducer holding apparatus 2.
Figure 7:
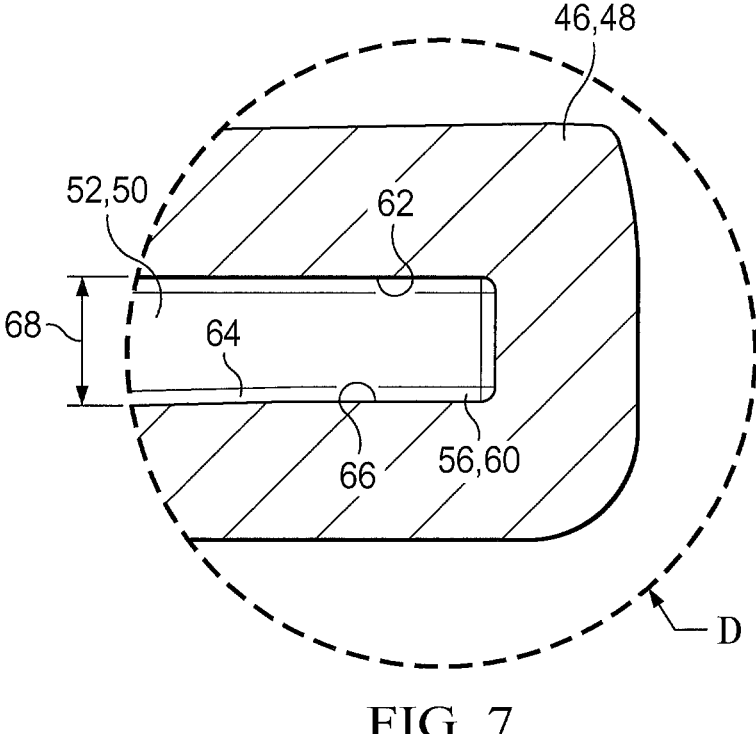
FIG. 7 is an enlarged view of the section D shown in FIG. 6.

As illustrated in FIGS. 6 and 7, each of the upwardly extending bracket slots 50 and 52 provided within the upwardly extending left and right brackets 46 and 48 of each transducer holder 18 has an upwardly extending rearward interior wall 62 and an upwardly extending forward interior wall 64. To assist in clipping a transducer 5 in the opposing pair of brackets 46 and 48 of each transducer holder 18, the forward interior wall 64, or at least a segment, e.g., of the lower half of the wall 64, of each of the bracket slots 50 and 52 will preferably taper rearwardly toward the rearward interior wall 62 as the forward interior wall 64 extends downwardly.

As the bracket slots 50 and 52 extend downwardly, the inward taper of the forward interior wall 64 of each of the bracket slots 50 and 54, or at least a segment, e.g., of the lower half of the wall 64, can continue all of the way to the closed bottom end 56 or 60 of the bracket slot 50 or 52 or can continue to a short clipping segment 66 of the bracket slot 50 or 52 at the bottom of the bracket slot 50 or 52. The short clipping segment 66 has a constant cross-sectional size and shape as it extends downwardly and has a height of not more than 20%, more preferably not more than 15% or not more than 10%, of the total height of the bracket slot 50 or 52.

Consequently, as the bracket slots 50 and 52 extend downwardly, the width 68 of each of the left and right bracket slots 50 and 52 between the forward interior wall 64 and the rearward interior wall 62 thereof decreases, at least in a segment, e.g., in the lower half of the bracket slot 50 or 52. The decrease in the width 68 of the bracket slot 50 or 52 can continue all of the way to the closed bottom end 56 or 60 of the bracket slot 50 or 52 or can continue to a short clipping segment 66, the short clipping segment 66 having a constant width 68 as it extends downwardly.

Figure 8:
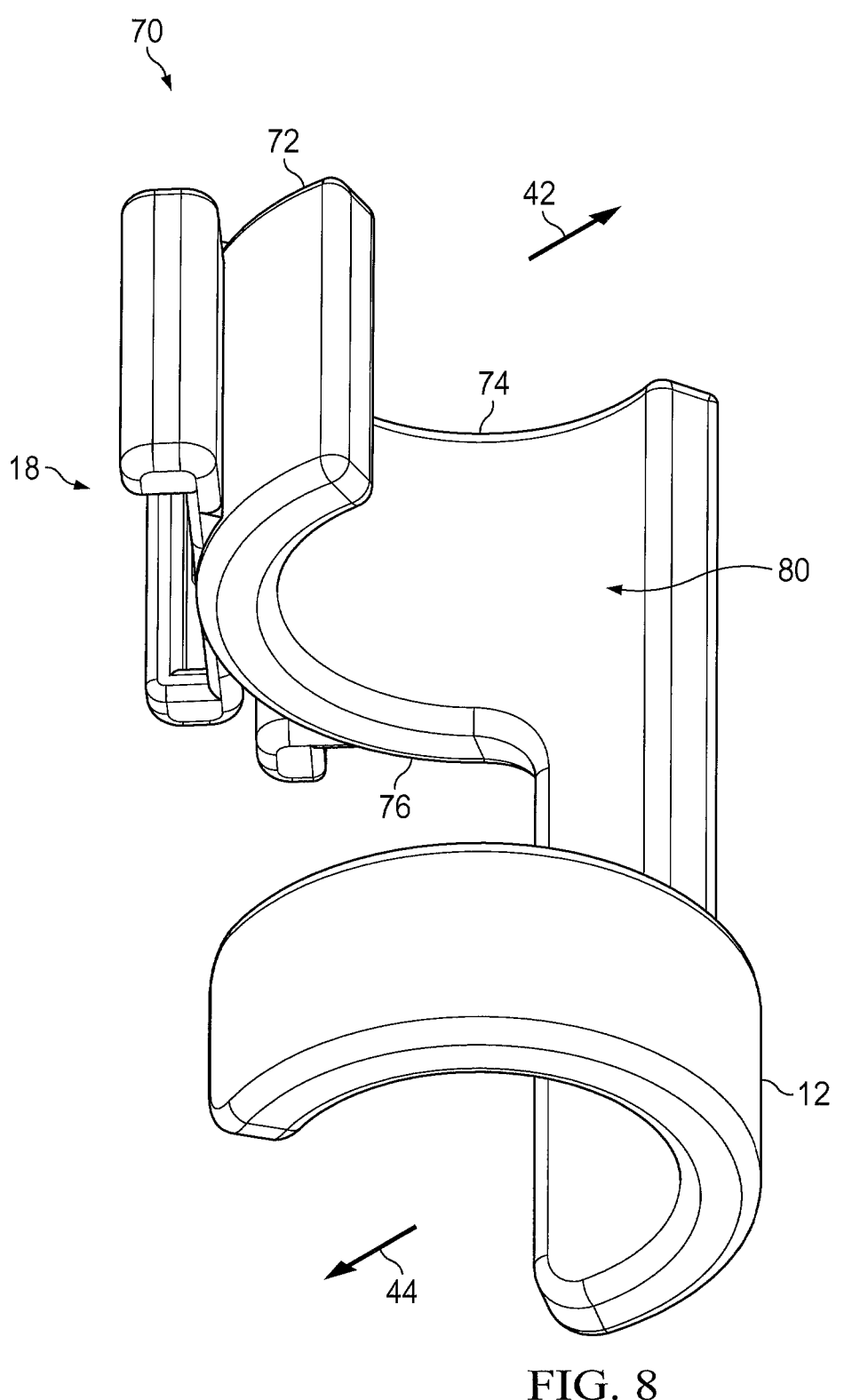
FIG. 8 is a perspective view of an alternative embodiment 70 of the apparatus provided by the present invention for holding pressure transducers on an IV pole.
Figure 9:
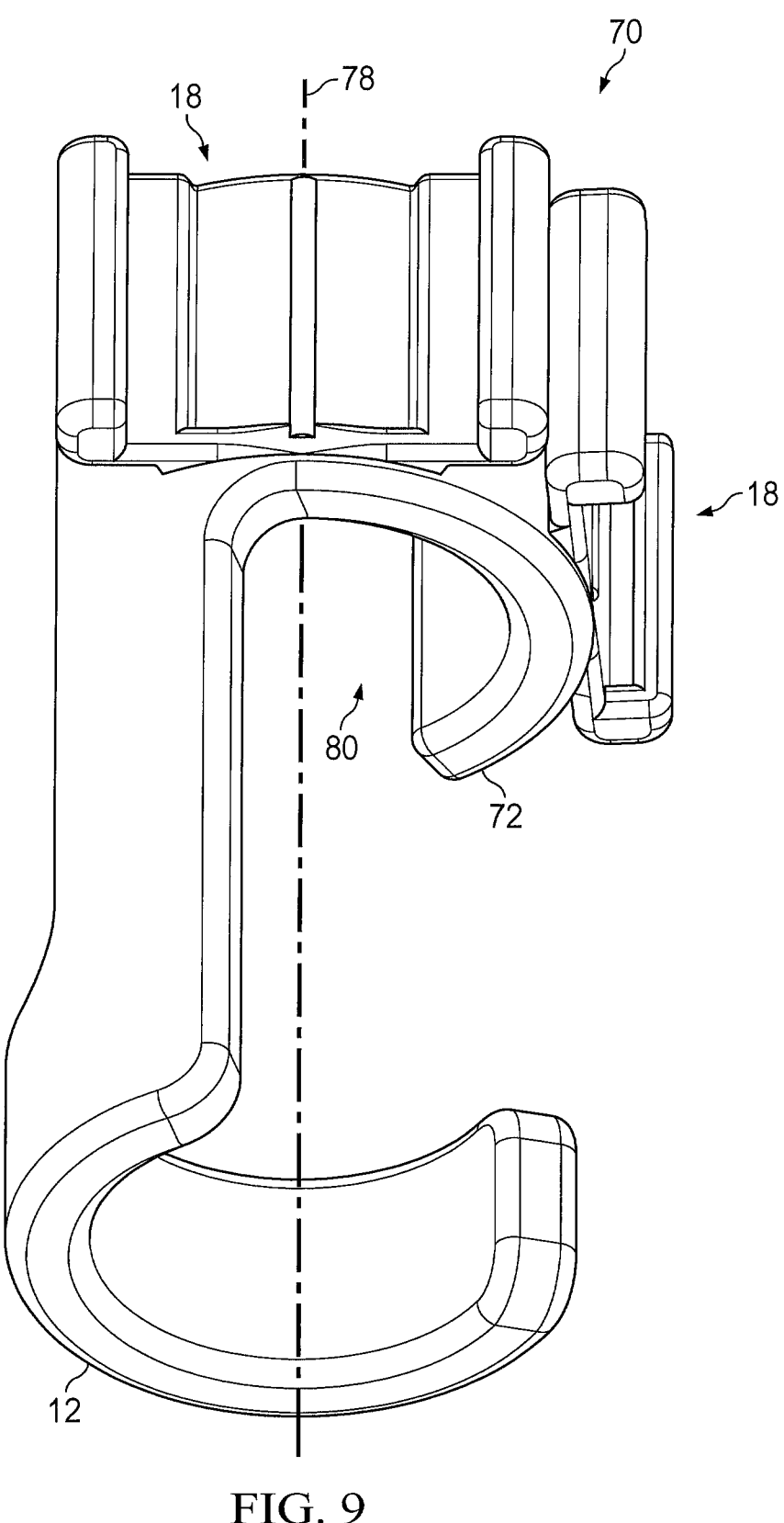
FIG. 9 is another perspective view of the inventive transducer holding apparatus 70.

An alternative embodiment 70 of the inventive apparatus for holding transducers 5 on an IV pole 6 is illustrated in FIGS. 8 and 9. The inventive holding apparatus 70 is identical to the inventive holding apparatus 2 except that the U-shaped collar 10 is replaced with a C-shaped semicircular collar 72 having one or more transducer holders 18, preferably two transducer holders 18, on the exterior of the C-shaped collar 72. The C-shaped collar 72 extends partially around the IV pole 6 and the longitudinal axis 78 of the inventive apparatus 70 and can be positioned at the upper longitudinal end or the lower longitudinal end of the holding apparatus 70. The C-shaped collar 72 preferably comprises an open top 74 and an open bottom 76, through which the longitudinal axis 78 and the IV pole 6 extend, and a side opening 80 for removably receiving the IV pole 6. The collar 72 preferably extends from about 170° to about 320° (i.e., within ±5°) around both (i) the longitudinal axis 78 of the inventive holder 2 and (ii) the IV pole 6. The collar 72 more preferably extends from about 180° to about 320° (i.e., within ±5°), or from about 180° to about 240°, around the longitudinal axis 78 and the IV pole 6.

The side opening 80 of the C-shaped collar 72 of the alternative apparatus 70 faces in the first radial direction 42 with respect to the longitudinal axis 78. The side gap opening 40 of the second collar 12 of the alternative apparatus 70 continues to face in the second radial direction 44, with respect to the longitudinal axis 78, which is preferably different from the first radial direction 42. For the alternative holding apparatus 70, the second radial direction 44 will preferably still be about 180° (i.e., 180°±5°) opposite the first radial direction 42.

Thus, the present invention is well adapted to carry out the objects and attain the ends and advantages mentioned above as well as those inherent therein. While presently preferred embodiments have been described for purposes of this disclosure, numerous changes and modifications will be apparent to those in the art. Such changes and modifications are encompassed within this invention as defined by the claims.

What is claimed is:

1. An apparatus for holding one or more transducers on an IV pole comprising:
   a longitudinal axis;
   a C-shaped first collar which has an arc in a range of from about 170° to about 320° and is receivable on the IV pole and extends partially around the longitudinal axis, the first collar having an open top and an open bottom through which the longitudinal axis extends and a side opening through which the IV pole is receivable;
   a second collar which is receivable on the IV pole and extends partially around the longitudinal axis, the second collar having an open top and an open bottom through which the longitudinal axis extends and a side opening through which the IV pole is receivable, and the second collar being positioned longitudinally below or above the first collar;
   a connecting arm which extends longitudinally from the first collar to the second collar;
   a first transducer holder which is integrally formed on an exterior of the first collar and tangential to the exterior of the first collar at a first location on the arc of the first collar;
   a second transducer holder which is integrally formed on the exterior of the first collar and tangential to the exterior of the first collar at a second location on the arc of the first collar which is different from the first location on the arc of the first collar so that the second transducer holder is oriented on the exterior of the first collar at an angle with respect to the first transducer holder; and
   each of the first and the second transducer holders comprising
      an upwardly extending left bracket;
      an upwardly extending right bracket;
      the upwardly extending left bracket comprising a left bracket slot which has an open upper end and a closed lower end;
      the upwardly extending right bracket comprising a right bracket slot which has an open upper end and a closed lower end; and
      the left bracket slot facing the right bracket slot.

2. The apparatus of claim 1 further comprising the second collar being a C-shaped collar.

3. The apparatus of claim 2 further comprising:
   the first collar extending from about 180° to about 320° around the longitudinal axis and
   the second collar extending from about 180° to about 320° around the longitudinal axis.

4. The apparatus of claim 1 further comprising:
   the side opening of the first collar facing a first radial direction with respect to the longitudinal axis and
   the side opening of the second collar facing a second radial direction with respect to the longitudinal axis which is different from the first radial direction.

5. The apparatus of claim 4 further comprising the second radial direction being about 180° opposite the first radial direction.

6. The apparatus of claim 1 further comprising for each of the transducer holders:
   the left bracket slot, or a segment of the left bracket slot, having a width, between a rearward interior wall and a forward interior wall of the left bracket slot, which decreases as the left bracket slot extends downwardly toward the closed lower end of the left bracket slot or to a clipping segment in a bottom end portion of the left bracket slot and
   the right bracket slot, or a segment of the right bracket slot, having a width, between a rearward interior wall and a forward interior wall of the right bracket slot, which decreases as the right bracket slot extends downwardly toward the closed lower end of the right bracket slot or to a clipping segment in a bottom end portion of the right bracket slot.

7. The apparatus of claim 6 further comprising for each of the transducer holders;
   the left bracket slot having the clipping segment in the bottom end portion of the left bracket slot;
   the width of the left bracket slot being constant in the clipping segment in the bottom end portion of the left bracket slot as the clipping segment in the bottom end portion of the left bracket slot extends downwardly;

the right bracket slot having the clipping segment in the bottom end portion of the right bracket slot; and the width of the right bracket slot being constant in the clipping segment in the bottom end portion of the right bracket slot as the clipping segment in the bottom end portion of the right bracket slot extends downwardly.

\* \* \* \* \*